United States Patent [19]

Korpman

[11] 4,413,995
[45] Nov. 8, 1983

[54] ABSORBENT PANEL SUITABLE FOR USE IN ABSORBENT PRODUCTS

[75] Inventor: Ralf Korpman, Bridgewater, N.J.

[73] Assignee: Personal Products Company, Milltown, N.J.

[21] Appl. No.: 380,646

[22] Filed: May 21, 1982

[51] Int. Cl.$^3$ .............................................. A61F 13/16
[52] U.S. Cl. ................................... 604/368; 428/283; 428/286; 428/287; 428/289; 428/913
[58] Field of Search ............... 428/407, 283, 286, 287, 428/289, 913; 604/368, 904

[56] References Cited

U.S. PATENT DOCUMENTS 2,992,149  7/1961  Drelich ............................... 428/237
4,333,464  6/1982  Nakano ............................... 428/407

Primary Examiner—William J. Van Balen
Attorney, Agent, or Firm—Martha A. Michaels

[57] ABSTRACT

The invention provides an absorbent panel which consists of a paper, film or fabric substrate coated on at least one surface with a reactive composition containing from 10 to 40 parts by weight of a liquid polyhydroxy organic compound and from 90 to 60 parts by weight of a particulate water-insoluble, water-swellable absorbent polymer having a gel capacity of at least 10. The absorbent panel is capable of absorbing at least 15 times its weight of liquid and is a thin structure.

17 Claims, 7 Drawing Figures

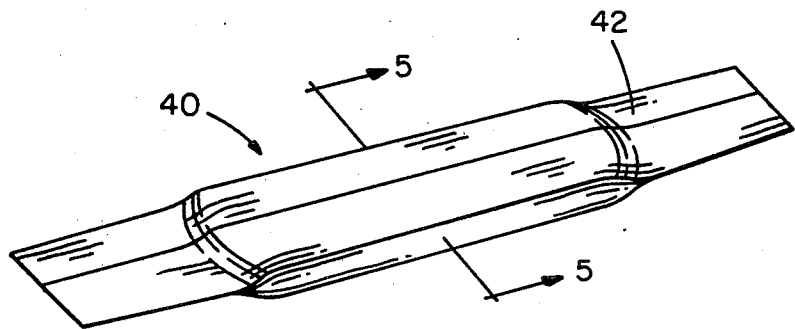
FIG. 4
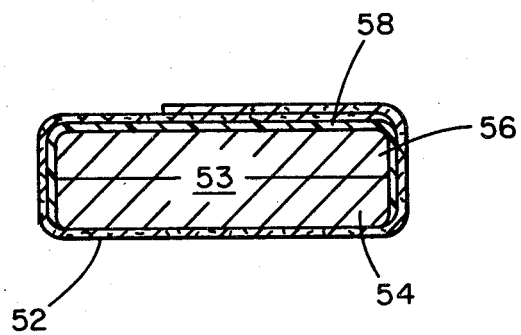
FIG. 5
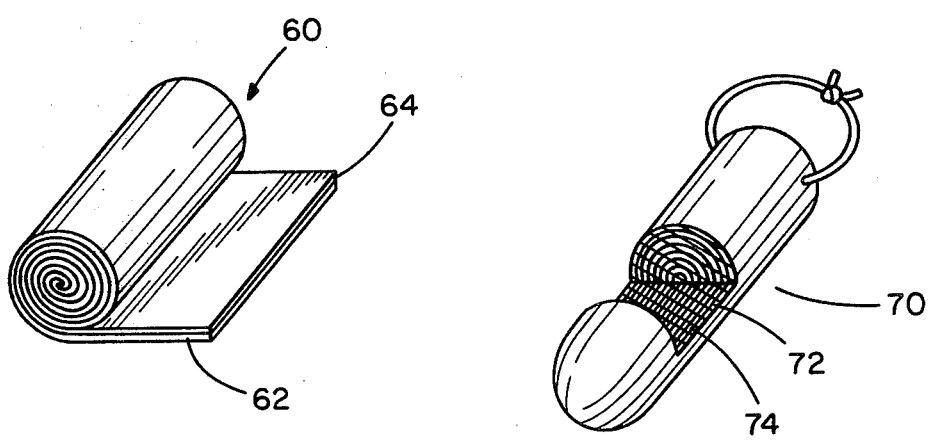
FIG. 6
FIG. 7

ABSORBENT PANEL SUITABLE FOR USE IN ABSORBENT PRODUCTS

BACKGROUND OF THE INVENTION

The present invention relates to an absorbent panel which is suitable for use in absorbent products such as incontinent pads, disposable diapers, sanitary napkins, tampons and the like. More particularly, the absorbent panel utilizes a superabsorbent composition.

Disposable absorbent products for body fluids are common-place in today's market. These products include incontinent pads, disposable diapers, sanitary napkins, tampons, adult incontinent systems and the like. Generally, in each of these products a fibrous batt is included which holds the liquid. These fibrous batts, although somewhat efficient, do not hold sufficient liquid or leak so as to cause a problem for the user. Superabsorbents, otherwise identified as hydrogels or hydrocolloids, have been incorporated in the fibrous batt structures and used in the articles mentioned above to increase their absorptive efficiency. The expected advantage of incorporating these materials which are in particulate form, is diminished by the shifting of the particulate materials in the articles during shipment and use by the wearer. Furthermore, the fibrous batts tend to be bulky and can provide discomfort to the wearer. A means of decreasing the mobility of the particulate absorbent materials and providing a structure which is not so bulky is desirable. U.S. Pat. No. 3,900,030 to Bashan describes a catamenial tampon which utilizes an open-celled polymer foam which has the water-swellable polymers imbedded therein. While this provides structural integrity to the absorbent polymer, versatility in application is governed by the foam carrier. Moreover, the method of disposition is dictated by the foam carrier.

SUMMARY OF THE PRESENT INVENTION

The present invention provides an absorbent panel which consists of a paper, film or fabric substrate coated on at least one surface with a reactive composition. The reactive composition contains from about 10 to about 40 parts by weight of a liquid polyhydroxy organic compound and from about 90 to about 60 parts by weight of a particulate water-insoluble, water-swellable absorbent polymer having a gel capacity of at least 10. Such an absorbent panel is capable of absorbing at least 15 times its weight of liquid or body fluid and yet is a relatively thin structure. The present invention also provides a method for making the absorbent panel and articles utilizing the absorbent panel.

BRIEF DESCRIPTION OF THE DRAWINGS

FIG. 4 is a perspective drawing of a sanitary napkin illustrating one embodiment of the present invention.

FIG. 5 is a cross-section view along lines 5—5 of FIG. 4.

FIG. 6 is a perspective view of a blank for a tampon illustrating one embodiment of the present invention.

FIG. 7 is a perspective view of a tampon with a portion broken away for illustrative purposes.

DETAILED DESCRIPTION OF THE INVENTION

Figure 1:
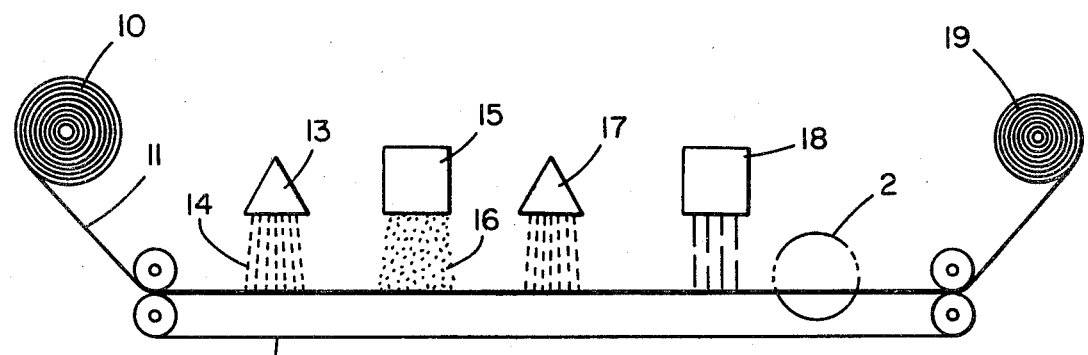
FIG. 1 is a schematic drawing of a method of manufacture of the absorbent panel of the present invention.

In accordance with the present invention, an absorbent panel is provided which comprises a paper, film, or fabric substrate coated on at least one surface with a reactive composition. The substrate coated with the reactive composition provides a relatively thin absorbent panel which can be used as supplementary to a fibrous batt in an absorbent product or in place of a fibrous batt in an absorbent product.

The reactive composition contains from about 10 to about 40 parts by weight of a liquid polyhydroxy organic compound and from about 90 to about 60 parts by weight of a particulate water-insoluble, water-swellable absorbent polymer having a gel capacity of at least 10.

The liquid polyhydroxy organic compound employed in the present invention is a liquid with a high boiling point having at least two hydroxy groups preferably vicinal or adjacent hydroxy groups. Suitable liquids include glycerol, ethylene glycol, propylene glycol and the like. Glycerol and ethylene glycol are preferred.

The water-insoluble, water-swellable absorbent polymer is generally a lightly cross-linked polymer containing a plurality of hydrophilic groups such as carboxyl, carboxamide, sulfonate salt or hydroxyl groups along the polymer chain in insufficient proportions so that the polymer would be water-soluble if it were not for the cross-linking thereof. In these polymers the hydrophilic groups constitute at least 25 percent and up to 72 percent of their molecular structure. The materials are of sufficient molecular weight or degree of cross-linking to be water-insoluble while water-swellable. Many of the materials are those which have been reported to have an average molecular weight per cross-linkage in the range of from about 13,000 to about 300,000 but are not limited thereto. The most common and best known of such materials are polyacrylate, modified polysaccharides, cross-linked synthetic polyacrylates, cross-linked carboxymethylcelluloses, or cross-linked poly(alkyleneoxide) as hereinafter defined. Other graft polymers of polysaccharides and natural gums such as xanthan gum, locust gum, guar gum and the like or blends thereof are also suitable provided they meet the requirements of water-insolubility and water-swellability. The water-insoluble, water-swellable polymers have a gel capacity of at least about 10. By "gel capacity" is meant the weight of aqueous fluid which can be imbibed and held per unit weight of polymer, i.e., grams of fluid per gram of polymer. Stated another way, the absorbent polymers have an absorbent capacity of at least 10 times the weight of the material in dry form. Commonly it is about 15 to 70 times the dry weight. The materials are frequently spoken of in the art as hydrogels, hydrocolloids, or superabsorbents. Many of the water-swellable polymers are available commercially.

The polymers are provided in particulate form. By "particulate" is meant a substance in the form of fine discrete particles. The particles may vary in shape such as spherical, rounded, angular, acicular, irregular, or fibrous. The particles generally range in size from about 1 micron to $2 \times 10^4$ microns in diameter or a cross-section (largest dimension when not spherical). The particles are preferably of finely divided powder of particle size from about 1 to about $10^3$ microns.

Referring now to the drawings, FIG. 1 schematically illustrates a method for preparing the absorbent panel of the present invention. In FIG. 1 a substrate, either paper, film, or fabric, is provided by a roll 10. The substrate 11 is conveyed by a conveyor 12 along a predetermined path. The liquid polyhydroxy organic compound 14 is sprayed by a spraying mechanism 13 onto one side of the substrate 11. The absorbent polymer 16 in powder form is applied in a substantially even layer with the desired amount on top of the liquid organic compound. More of the liquid polyhydroxy organic compound is applied by a sprayer 17 on top of the powdered absorbent polymer. The reactive composition which has formed on the substrate is then subjected to heat, if desired, by a heat unit 18 which raises the temperature of the reactive mixture to between 200° and 400° F. to allow the reactive composition to fuse. The substrate containing the coating, thus forming the absorbent panel of the present invention, is then rolled on a roll 19 for storage until the desired time of use. The absorbent panel in the form of a strip may be cut into the desired shapes and sizes for its subsequent use.

Figure 2:
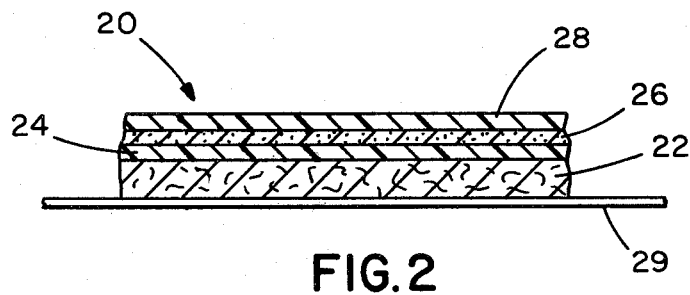
FIG. 2 is an enlarged portion from FIG. 1 illustrating a fraction of the absorbent panel of the present invention.

Referring now to FIG. 2, a fragment of the absorbent panel is shown. This fragment 20 consists of the substrate 22, a layer of liquid polyhydroxy organic compound 24, a layer of absorbent polymer 26 and a final layer of liquid polyhydroxy organic compound 28. Reaction has taken place between the organic compound and the absorbent polymer which reaction in this particular instance has been fused by heat, however, heat is used only to speed the fusion. The resulting layers have formed a film on the substrate which film is flexible and permanently affixed to the substrate. Thus the absorbent polymer is securely fixed in position on the absorbent panel.

Figure 3:
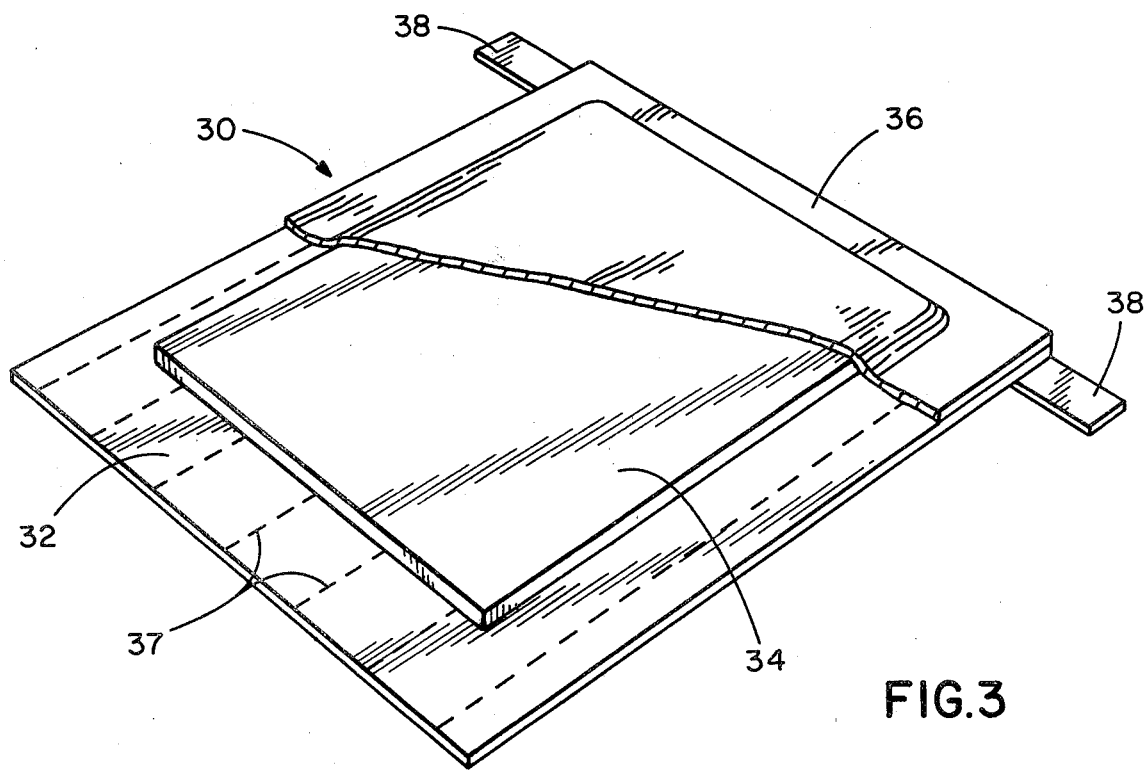
FIG. 3 is a perspective view of a disposable diaper with a portion broken away for clarity illustrating one embodiment of the present invention.

In FIG. 3 a perspective view is shown of a disposable diaper 30 with a portion broken away for clarity. A moisture impermeable backing 32 is provided upon which is placed an absorbent panel 34. The absorbent core is an absorbent panel of the present invention. The upper surface of the diaper consists of a facing sheet 36 which is moisture-permeable. The facing sheet and backing sheet are held together in the margin by glue lines 37. These glue lines also assist in maintaining the position of the absorbent panel in the diaper structure. Tape tabs 38 are provided for securing the diaper about the wearer.

FIG. 4 illustrates a sanitary napkin 40 having a cover wrap 42. FIG. 5 is a cross-sectional view along lines 5—5 of the sanitary napkin illustrated in FIG. 4. The cover wrap 52 is generally a moisture-permeable nonwoven fabric. The absorbent core 53 in this instance consists of a fibrous absorbent batt 54 and an absorbent panel 56 of the present invention. A moisture-impermeable barrier sheet 58 is provided to prevent leakage when the absorbent core becomes somewhat saturated.

FIG. 6 provides a tampon blank 60, which when rolled and placed in a tampon forming process, produces a tampon such as appears in FIG. 7. The blank 60 is provided with an absorbent batt layer 62 and an absorbent panel 64 from the present invention. These layers are merely placed adjacent one another and rolled as illustrated. In FIG. 7 the fibrous batt 72 and the absorbent panel 74 appear adjacent one another in roll form as illustrated in the broken away portion of the figure.

Many water-insoluble, water-swellable polymers suitable as absorbent are available commercially. They also may be prepared by cross-linking a pre-formed water-soluble, straight chain polymer, by polymerizing an appropriate monomer or a monomer with a comonomer to effect simultaneous polymerization and cross-linking, or by incorporating a hydrophilic group into a completed polymer. An example of a later incorporation of a hydrophilic group to the completed polymer is the incorporation by sulfonation of a sulfonic acid moiety. When it is desired to have the hydrophilic group in the salt form, the polymer may be prepared first as an acid, ester, amide, or nitrile and the product hydrolyzed in whole or in part.

The preferred polymers have an acrylate group in their molecular structure. They may be completely synthetic acrylate polymers or acrylate modified polysaccharides, e.g., acrylate modified starch or acrylate modified cellulose. By "acrylate modified" is meant that an acrylate polymer or polyacrylate as hereinafter described has been grafted onto the polysaccharide. "Acrylate polymer" or "polyacrylate" as herein employed embraces not only polymers which contain acrylate salt groups but those which also may contain an acrylamide, acrylic acid, acrylic ester group or acrylonitrile group.

The preferred synthetic acrylate polymer absorbents are those which have a salt group, an acid group, or which have both an amide group and a salt or acid group. These have been represented in the literature, e.g., U.S. Pat. No. 3,686,024, by the following formula:

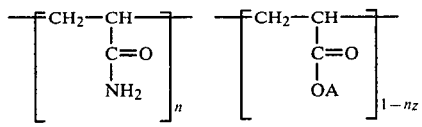

where A is an alkali metal ion such as sodium or potassium, or is hydrogen, n is from about 0.5 to about 0.9, 1-n defines the extent of hydrolysis, and z is the number of mer units between cross-links.

The polyacrylate absorbent containing both amide and carboxylate groups may be prepared either (1) by aqueous polymerization of acrylamide with a difunctional organic cross-linker such as N,N'-methylenebisacrylamide in the presence of a free radical catalyst to obtain a water-swellable, cross-linked polyacrylamide, followed by partial hydrolysis in aqueous alkali to obtain a cross-linked polymer having both an amide and an alkali metal carboxylate groups as more fully described in U.S. Pat. No. 3,247,171, or (2) by copolymerization of acrylamide and acrylic acid alkali metal salt in the presence of a cross-linking monomer such a N,N'-methylenebisacrylamide and a catalyst system such as 1:1 ammonium persulfate and β-dimethyl-aminopropionitrile, also described in the aforesaid patent, or (3) by radiation polymerization and cross-linking as described in U.S. Pat. No. 4,192,727.

Polyacrylate absorbents also may be prepared by subjecting linear polyacrylate to high energy radiation cross-linking as described in U.S. Pat. No. 3,229,769, or to chemical polymerization and cross-linking as described in British Pat. No. 719,330, or may be prepared by cross-linking of a previously prepared polyacrylamide.

Acrylate modified polysaccharides are those which have a polyacrylate chain grafted onto a cellulose or starch molecule. They are preferred graft copolymers of polysaccharides which have hydrophilic chains grafted thereon. By "hydrophilic chain" is meant a polymer chain obtained from monomers which have a group which is water-soluble or becomes water-soluble on hydrolysis, e.g., carboxyl, sulfonic, hydroxyl, amide, amino, quaternary ammonium and hydrolysis products thereof. In the polysaccharides acrylate polymers, a hydrophilic chain of the general formula

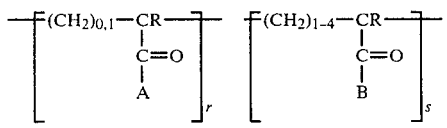

is attached to the backbone of the cellulose or starch molecule through a carbon linkage. In the formula,

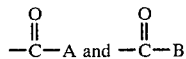

independently represents an acid, ester, alkali metal, ammonium salt or amide group, each R independently is hydrogen or lower alkyl, r is an integer of from 0 to about 5,000 and s is an integer of from 0 to about 5,000, and r+s is at least 500.

The polysaccharide acrylate polymers may be prepared employing well known procedures for carrying out graft copolymerization of olefinically unsaturated chains onto cellulose and starch in which grafting of the hydrophilic material onto a starch or cellulose backbone is accomplished simultaneously with the formation of the hydrophilic polymeric material, and, if necessary, followed by hydrolysis. Thus, the polymers may be prepared by the polymerization of an appropriate polysaccharide with an appropriate acrylic monomer such as acrylonitrile, methacrylonitrile, methyl or ethyl acrylate, acrylic or methacrylic acid, or with acrylamide or methacrylamide, followed by alkaline hydrolysis or by the polymerization of alkali metal salt of acrylic or methacrylic acid with the appropriate polysaccharide.

The polymerization is carried out in the presence of a free radical catalyst system in an aqueous medium, or by irradiation (ultra-violet, gamma-, or X-radiation). Catalyst systems for employment in aqueous media usually comprise an inorganic oxidizing agent as initiator and an inorganic reducing agent as activator. Representative oxidizing agent initiators are inorganic persulfates, peroxides and alkali metal bromates and chlorates. Representative reducing agent activators are alkali metal bisulfites, sulfites, ferrous ammonium sulfate, and alkali metal thiosulfate.

In a method for carrying out graft polymerization employing a catalyst system, the inorganic oxidizing agent initiator and the inorganic reducing agent activator each as an aqueous solution are alternately added to a reaction medium comprising a water-solution of an acrylate monomer, a co-monomer, a cross-linking monomer, and a dispersion of pulverulent or fibrous water-insoluble, water-swellable polysaccharide in water-immiscible organic liquid containing a minor amount of water-miscible solvent to obtain an acrylate modified polysaccharide product as more fully described in U.S. Pat. No. 4,028,290. Other suitable methods for chemical catalytic graft polymerization may be found in U.S. Pat. Nos. 3,256,372; 3,661,815; 4,076,663; 3,889,678 and 4,105,033.

Suitable polysaccharide acrylate polymers are those in which the hydrophilic chain loading on the backbone is in the range of from about 10 percent by weight to about 90 percent by weight, usually from about 40 to 80 percent by weight of the polysaccharide acrylate polymer.

Other suitable water-insoluble, water-swellable polymers include cross-linked carboxymethylcellulose (CMC) obtained as described, for example, in U.S. Pat. No. 2,639,239, cross-linked poly(alkylene oxide) of molecular weight of at least 100,000, obtained as described, for example, in U.S. Pat. Nos. 3,956,224; 3,264,202; 3,957,605 and 3,898,143; and blends of organic substances of polysaccharide character, e.g., natural or synthetic gums. It has been found generally that when gums are employed they must be employed as blends. It appears that the polysaccharide gums which are normally soluble interact when employed as blends to have the desirable swellability without the undesirable solubility. Typical gums which may be employed in blends include locust bean gum, guar gum, xantham gum, tragacanth gum, karaya gum and the like. Gum blends as well as the absorbent polymers above described are available commercially under various trade names.

The water-insoluble, water-swellable polymers prepared by any of the foregoing methods are generally obtained as stiff, brittle solids. These may be comminuted to the appropriate size. Preferably they are employed in the form of powder as previously defined, but may also be employed in other forms.

The liquid polyhydroxy compounds which are suitable from the currently available hydroxy compounds are quite limited and are substantially as previously defined. To reiterate these polyhydroxy organic compounds have a high boiling point and generally include glycerol, ethylene glycol, propylene glycol and the like.

The reactive composition formed by the combination of the liquid polyhydroxy organic compound and the absorbent polymer is formed in a number of ways. Previously illustrated is the method of spraying the liquid onto a substrate and spreading the polymer in powder form followed by another liquid layer on top of the powder. This is sufficient contact to permit the reactive composition to react and adhere to the substrate so as to form the absorbent panel. When applying the components stepwise it is not required to place a liquid layer on the substrate first. In other words, that step may be eliminated and the procedure would simply be spreading the powder onto the substrate and then spraying a liquid layer over the powder.

As mentioned heretofore, the substrate may be either paper, film, or fabric. It is preferred that a paper substrate be a relatively soft flexible receptive substrate. In other words, a high polished slick paper would not be as suitable because of its stiffness and it would not be as receptive to the reactive composition as a softer, more porous paper. An example of a suitable paper substrate is tissue. The film substrate may be any known film, preferably one with integrity and flexibility. The fabric substrate may be a woven textile or a nonwoven fabric such as a polyester, polypropylene or polyethylene fabric. It is preferred that the fabric be moisture permeable so that the entire substrate is utilized as a part of the absorbent panel. The amount of the reactive mixture applied to the substrate will vary according to the absorption required in the ultimate environment. It may be desirous to make the reactive composition layer sufficiently thin so as to prevent gel blocking when the absorbent polymer is receiving liquid. By "gel blocking" is meant particles of absorbent polymer sufficiently close that when they swell they make contact with one another and form a substantially continuous layer of a gel which would be impervious to subsequent liquid or moisture. In some instances of use, it may not be necessary for gel blocking to be avoided and consequently a relatively large amount of the reactive composition can be applied to the substrate.

For forming the absorbent panels mentioned above used in diapers, sanitary napkins, tampons and the like, it is recommended that the reactive mixture be applied in an amount ranging from about 10 to about 250 gm/square meter.

The following examples are illustrative of the present invention.

EXAMPLES 1-5

Reaction compositions were prepared on tissue substrate according to the formulations shown in Table I below. All parts are in parts by weight.

TABLE I

| COMPONENTS | EXAMPLES (Parts by Weight) | | | | |
|---|---|---|---|---|---|
| | 1 | 2 | 3 | 4 | 5 |
| Glycerol | | | | 15 | 25 |
| Ethylene Glycol | 15 | 25 | 10 | | |
| Permasorb 20 (cross-linked ionic polyacrylate, National Starch) | 85 | | | | |
| Sanyo 300 (polyacrylate, Sanyo) | | 75 | | 85 | |
| Henkel 147 (starch polyacrylate, Henkel) | | | 90 | | 75 |

Approximately one-half of the polyhydroxy organic compound was sprayed onto the tissue substrate. The absorbent polymer was then sprinkled evenly on the organic compound and the remaining organic compound was sprayed on top of the absorbent polymer. The resulting reaction composition was subjected to a temperature of 200° F. for about 10 seconds to enhance fusion of the reaction composition.

The foregoing description and the drawings are illustrative and are not to be taken as limiting. Still other variations and modifications are possible without departing from the spirit and scope of the present invention.

I claim:

1. An absorbent panel comprising a paper or fabric substrate coated on at least one surface thereof with a reactive composition of from about 10 to about 40 parts by weight of a liquid polyhydroxy organic compound and from about 90 to about 60 parts by weight of a particulate water-insoluble, water-swellable absorbent polymer having a gel capacity of at least 10.

2. The absorbent panel of claim 1 wherein the liquid polyhydroxy organic compound is selected from the group consisting of glycerol, ethylene glycol and propylene glycol.

3. The absorbent panel of claim 1 wherein the absorbent polymer is a polyacrylate.

4. The absorbent panel of claim 1 wherein the substrate is paper.

5. The absorbent panel of claim 1 wherein the substrate is a fabric.

6. The absorbent panel of claim 5 wherein the fabric is a nonwoven fabric.

7. The absorbent panel of claim 6 wherein the nonwoven fabric is polyester.

8. An absorbent panel comprising a nonwoven fabric coated on at least one surface thereof with a reactive composition of from about 20 to about 30 parts by weight of a liquid polyhydroxy organic compound and from about 80 to about 70 parts by weight of a particulate water-insoluble, water-swellable absorbent polymer having a gel capacity of at least 10.

9. A disposable absorbent structure containing an absorbent core comprising an absorbent panel having a paper or fabric substrate coated on at least one surface with a reactive composition of from about 10 to about 40 parts by weight of a liquid polyhydroxy organic compound and from about 90 to about 60 parts by weight of a particulate water-insoluble, water-swellable absorbent polymer having a gel capacity of at least 10.

10. The absorbent structure of claim 9 wherein the absorbent core comprises said absorbent panel and a lightly compacted cellulosic fibrous batt in juxtaposition with said absorbent panel.

11. A disposable diaper having a moisture-impermeable backing and absorbent core and a moisture-permeable facing sheet said absorbent core being sandwiched between said facing sheet and said backing sheet, the improvement comprising an absorbent core containing a paper or fabric substrate coated on at least one surface with a reactive composition of from about 10 to about 40 parts by weight of a liquid polyhydroxy organic compound and from about 90 to about 60 parts by weight of a particulate water-insoluble, water-swellable absorbent polymer having a gel capacity of at least 10.

12. A sanitary napkin containing an absorbent core comprising a paper or fabric substrate coated on at least one surface with a reactive composition of from about 10 to about 40 parts by weight of a liquid polyhydroxy organic compund and from about 90 to about 60 parts by weight of a particulate water-insoluble, water-swellable absorbent polymer having a gel capacity of at least 10.

13. The sanitary napkin of claim 12 wherein the absorbent core comprises a loosely-compacted, cellulosic, fibrous batt and said absorbent panel placed in juxtaposition one to the other.

14. The sanitary napkin of claim 12 wherein the absorbent core comprises said absorbent panel surrounded by a loosely-compacted cellulosic fibrous batt.

15. A tampon containing an absorbent core comprising a paper or fabric substrate coated on at least one surface with a reactive composition of from about 10 to about 40 parts by weight of a liquid polyhydroxy organic compound and from about 90 to about 60 parts by weight of a particulate water-insoluble, water-swellable absorbent polymer having a gel capacity of at least 10.

16. A process for preparing an absorbent panel comprising:
(a) providing a paper, film, or fabric substrate with a thin layer of a particulate water-insoluble, water-swellable absorbent polymer having a gel capacity of at least 10;
(b) coating the substrate on the side of the layer of particulate polymer with a liquid polyhydroxy organic compound to provide a reactive composition on the substrate, the composition containing from about 10 to about 40 parts by weight of said organic compound and from about 90 to about 60 parts by weight of said particulate polymer; and (c) fusing said reactive composition.

17. The process of claim 16 wherein said reactive composition is present on said substrate in an amount from about 10 to about 250 grams per square meter.

* * * * *